United States Patent
Ratilainen et al.

(10) Patent No.: US 6,362,211 B2
(45) Date of Patent: Mar. 26, 2002

(54) POLYCYCLIC INDANYLIMIDAZOLES WITH ALPHA2 ADRENERGIC ACTIVITY

(75) Inventors: Jari Ratilainen, Joensuu; Paavo Huhtala, Espoo; Arto Karjalainen, Espoo; Arja Karjalainen, Espoo; Antti Haapalinna, Turku; Raimo Virtanen, Rusko; Jyrki Lehtimäki, Sauvo, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/849,540

(22) Filed: May 7, 2001

(30) Foreign Application Priority Data

May 8, 2000 (FI) .............................. 20001065

(51) Int. Cl.$^7$ ................. A61K 31/4164; C07D 233/54; C07D 233/56
(52) U.S. Cl. ................... 514/396; 514/399; 548/341.1; 548/345.1
(58) Field of Search ........................ 548/341.1, 345.1; 514/396, 399

(56) References Cited

U.S. PATENT DOCUMENTS 5,658,938 A    8/1997    Geerts et al.

FOREIGN PATENT DOCUMENTS

| EP | 0 183 492 | 7/1986 |
| EP | 0 247 764 | 12/1987 |
| EP | 0 372 954 | 6/1990 |
| WO | WO 97/12874 | 4/1997 |

OTHER PUBLICATIONS

Dehmlow et al., "Über die Bildung von Indanonderivaten bei der Pyrolyse von 3–Phenylpropionylchloriden", Liebigs Ann. Chem. pp. 1617–1624 (1977).

Manyik et al., "Improvement of Boron Fluoride Method of Acylation of Ketones to Form β–Diketones. Ring Opening of 2–Acyl Cylic Ketones to Form Keto Acids$^1$", Am. Chem. Soc. vol. 75, pp. 5030–5032 (1953).

Ranu et al., "A New Redundant Rearrangement of Aromatic Ring Fused Cyclic α–Hydroxydithiane Derivatives. Synthesis of Aromatic Ring Fused Cyclic 1,2–Diketones with One–Carbon Ring Expansion", J. Org. Chemo vol. 64, pp. 6380–6386 (1999).

Kaye et al., "Asymmetric Simmons–Smith Cyclopropanation of α,β–Unsaturated Bornane–2,3–Diol Acetals", Synthetic Communications, vol. 29(11), pp. 1889–1902 (1999).

House et al., "The Synthesis of Hexahydrofluorenone Derivatives", J. Am. Chem. Soc., vol. 82, pp. 1457–1462 (1960).

Hansen et al., "A Synthesis of the Indano–[1,2–b] aziridine System", Acta Chem. Scand., vol. 27, No. 3. pp. 1112–1113 (1973).

Ghosh et al., "Benzocycloenones as Dienophiles. Stereocontrolled Synthesis of Benzohydropentalene and Benzohydroazulene", Tetrahedron, vol. 41, No. 2, pp. 349–355 (1985).

Thiele et al., "Ueber Condensationsproducte des o–Phtalaldehyds", Liebigs Ann. Chemie, vol. 347, pp. 112–131 (1906), copy of co–pending application No. 09/051,151, filed on Apr. 2, 1998.

Copy co–pending application No. 09/051,151, filed on Apr. 2, 1998.

*Primary Examiner*—Laura L. Stockton
(74) *Attorney, Agent, or Firm*—Finnegan, Henderson, Farabow, Garrett & Dunner, L.L.P.

(57) ABSTRACT

A compound of formula I

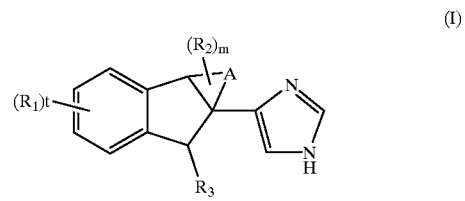

wherein $R_1$ to $R_3$, —A—, m and t are as defined in claim 1, or a pharmaceutically acceptable salt or ester thereof, useful as an alpha2 adrenergic agent.

16 Claims, No Drawings

POLYCYCLIC INDANYLIMIDAZOLES WITH ALPHA2 ADRENERGIC ACTIVITY

CROSS REFERENCE TO RELATED APPLICATIONS

This application claims the benefit of foreign priority under 35 U.S.C. §119(a) to Finnish patent application no. 20001065, filed on May 8, 2000, the contents of which are incorporated by reference herein.

BACKGROUND OF THE INVENTION

The present invention relates to new pharmacologically active polycyclic indanylimidazole derivatives and pharmaceutically acceptable salts and esters thereof, as well as to pharmaceutical compositions containing them.

It is known that several derivatives of imidazole have affinity for alpha1 and/or alpha2 adrenoceptors. Accordingly, for example, WO-A-97 12874 describes imidazole-substituted (1,2,3,4-tetrahydro-1-naphthalenyl)- and (2,3-dihydro-1H-inden-1-yl)-derivatives which are stated to possess affinity for alpha2 adrenoceptors, most of them being selective alpha2 adrenoceptor agonists. EP-A-0 717 037 describes 4-(1,2,3,4-tetrahydro-1-naphthalenyl)- and 4-(2,3-dihydro-1H-inden-1-yl)-1H-imidazole derivatives which possess alfa2 adrenoceptor agonistic and alpha1 adrenoceptor antagonistic activity. Furthermore, the imidazole derivatives disclosed in EP-A-0 183 492 are known as alpha2 adrenoceptor antagonists. Compounds acting on the said alpha adrenoceptors may exert a wide variety of peripheral and/or CNS (central nervous system) effects in mammals.

SUMMARY OF THE INVENTION

The inventors have now found that the present polycyclic indanylimidazole derivatives of the invention exhibit affinity for alpha2 adrenoceptors so that they can be useful in the treatment of various diseases or conditions wherein the alpha2 adrenoceptors are involved. Such diseases or conditions include various disorders of the central nervous system (CNS), i.e. neurological, psychiatric or cognition disorders, as well as various disorders of the peripheric system, e.g. diabetes, orthostatic hypotension, lipolytic disorders (such as obesity) or sexual dysfunction.

DETAILED DESCRIPTION OF THE INVENTION

The polycyclic indanylimidazole derivatives of the invention can be represented by the following formula (I):

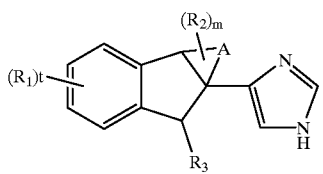

(I)

wherein

—A— forms, together with the two carbon atoms to which it is attached, a ring system being a partially or fully saturated monocyclic carbocyclic ring of 3 to 7 ring atoms or a partially or fully saturated bicyclic bridged carbocyclic ring of 6 to 10 ring atoms, wherein each of the said ring systems formed by —A— is optionally fused with a benzene ring which is optionally substituted with one to three substituent(s) $R_1$;

each $R_1$ is independently halogen, OH, $NH_2$, $(C_{1-6})$alkyl, $(C_{2-6})$alkenyl, $(C_{2-6})$alkynyl, $(C_{1-6})$alkoxy, halo-$(C_{1-6})$alkyl, OH—$(C_{1-6})$alkyl, mono- or di$(C_{1-6})$alkylamino or OH—$(C_{1-6})$alkoxy$(C_{1-6})$alkoxy;

each $R_2$ is independently halogen, OH, =O, =$CH_2$, $NH_2$, $(C_{1-6})$alkyl, $(C_{2-6})$alkenyl, $(C_{1-6})$alkoxy, halo-$(C_{1-6})$alkyl, OH—$(C_{1-6})$alkyl, $NH_2$—$(C_{1-6})$alkyl or mono- or di$(C_{1-6})$alkylamino;

$R_3$ is H, F, OH, =O, =$CH_2$, $(C_{1-6})$alkyl, $(C_{2-6})$alkenyl, $(C_{2-6})$alkynyl, $(C_{1-6})$alkoxy, halo-$(C_{1-6})$alkyl, $NH_2$ or mono- or di$(C_{1-6})$alkylamino;

m is 0, 1, 2 or 3; and t is 0, 1, 2 or 3;

or a pharmaceutically acceptable ester or salt thereof.

The invention also includes mixtures of compounds defined above.

In one possible subgroup of compounds of formula (I), the said ring formed by —A— is a fully saturated monocyclic carbocyclic ring moiety of 3, 4, 5, 6 or 7 ring atoms, e.g. cyclopropa, cyclobuta, cyclopenta, cyclohexa or cyclohepta, such as cyclopropa, cyclopenta, cyclohexa or cyclohepta, fused to the indane backbone structure. In another possible subgroup of the compounds of formula (I), —A— forms a fused, partially saturated monocyclic carbocyclic ring system of 5, 6 or 7 ring atoms, which contains one double bond, e.g. a fused cyclopentene or cyclohexene ring. The said fully or partially saturated carbocyclic ring system fused to the indan backbone can optionally be substituted with one to three, e.g. one or two, such as one, substituent(s) $R_2$ as defined above, and/or further be fused with an unsubstituted benzene ring or with a benzene ring substituted with one to three substituents $R_1$ as defined above.

In another possible subgroup of the compounds of formula (I), —A— forms a fused, fully or partially saturated bicyclic bridged carbocyclic ring system of 6 to 10 ring atoms, e.g. of 7 or 8 ring atoms, such as a fused bicyclo [2.2.1]heptane or bicyclo[2.2.2]octane ring. The said bridged carbocyclic ring moiety can optionally be substituted with one to three, e.g. one or two, such as one, substituent(s) $R_2$ as defined above and/or further be fused with an unsubstituted benzene ring or with a benzene ring substituted with one to three substituents $R_1$ as defined above.

The following subgroups (1) to (6) of compounds of formula I taken alone or in any combination with each other are possible, (1) m is 0 or 1; e.g. 0

(2) m is 1 and $R_2$ is halogen, OH, =O, $NH_2$, =$CH_2$, $(C_{1-6})$alkyl, $(C_{2-6})$alkenyl, $(C_{1-6})$alkoxy, halo-$(C_{1-6})$alkyl, OH—$(C_{1-6})$alkyl, $NH_2$—$(C_{1-6})$alkyl or mono- or di$(C_{1-6})$alkylamino; e.g. OH, =O, =$CH_2$, $(C_{1-6})$alkyl, or $(C_{1-6})$alkoxy; e.g. OH, =O, =$CH_2$ or $(C_{1-6})$alkyl; such as $(C_{1-6})$alkyl or =$CH_2$;

(3) t is 0 or 1; e.g. 0;

(4) t is 1 and $R_1$ is selected from halogen, OH, $NH_2$, $(C_{1-6})$alkyl, $(C_{2-6})$alkenyl, $(C_{2-6})$alkynyl, $(C_{1-6})$alkoxy, halo-$(C_{1-6})$alkyl, OH—$(C_{1-6})$alkyl, mono- or di$(C_{1-6})$alkylamino or OH—$(C_{1-6})$alkoxy$(C_{1-6})$alkoxy; e.g. halogen, OH, $(C_{1-6})$alkyl, $(C_{1-6})$alkoxy and OH—$(C_{1-6})$alkoxy$(C_{1-6})$alkoxy; such as halogen, e.g. F, OH, $(C_{1-6})$alkoxy and OH—$(C_{1-6})$alkoxy$(C_{1-6})$alkoxy;

(5) $R_3$ is selected from H, OH, =O, =$CH_2$, $(C_{1-6})$alkyl, $(C_{2-6})$alkenyl and $(C_{1-6})$alkoxy; e.g. H, OH, =O, =$CH_2$ and $(C_{1-6})$alkyl; such as H, OH and =O; e.g. H; and (6) the —A— ring fused to the indan ring is further fused with an unsubstituted benzene ring or a benzene ring substituted with one to three, e.g. one, substituents $R_1$ as defined above, e.g. under (4).

A possible subgroup of the compounds of formula I are compounds of formula Ia

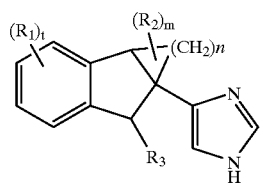

Ia wherein $R_1$, $R_2$, $R_3$, m and t are as defined above and n is 1,2,3, 4 or 5.

In a subgroup of compounds Ia, m is 0. In another subgroup of compounds Ia, m is 1 and $R_2$ is selected from halogen, OH, =O, =$CH_2$, $(C_{1-6})$alkyl and $(C_{1-6})$alkoxy; e.g. OH, =O, =$CH_2$ and $(C_{1-6})$alkyl; such as $(C_{1-6})$alkyl and =$CH_2$. In a further subgroup of compounds Ia, t is 0. In another subgroup of compounds Ia, t is 1 and $R_1$ is selected from halogen, OH, $(C_{1-6})$alkyl, $(C_{1-6})$alkoxy and OH—$(C_{1-6})$alkoxy$(C_{1-6})$alkoxy; such as halogen, OH, $(C_{1-6})$alkoxy and OH—$(C_{1-6})$alkoxy$(C_{1-6})$alkoxy; such as halogen, e.g. F, OH and $(C_{1-6})$alkoxy. In a subgroup of compounds Ia, $R_3$ is selected from H, OH, =O, $(C_{1-6})$alkyl, $(C_{2-6})$alkenyl and $(C_{1-6})$alkoxy; e.g. H, OH, =O and $(C_{1-6})$alkyl; such as H, OH and =O; e.g. H. In one embodiment of the compounds of formula Ia, the carbocyclic ring fused to the indan ring is further fused with an unsubstituted or substituted benzene ring. The substituted benzene ring bears one to three, e.g. one, substituent(s) $R_1$ as defined above; e.g. each $R_1$ is independently halogen, OH, $(C_{1-6})$alkyl, $(C_{1-6})$alkoxy or OH—$(C_{1-6})$alkoxy$(C_{1-6})$alkoxy; such as halogen, OH, $(C_{1-6})$alkoxy and OH—$(C_{1-6})$alkoxy$(C_{1-6})$alkoxy alkoxy; such as halogen, e.g. F, OH or $(C_{1-6})$alkoxy.

Another possible subgroup of the compounds of formula I are compounds of formula Ib

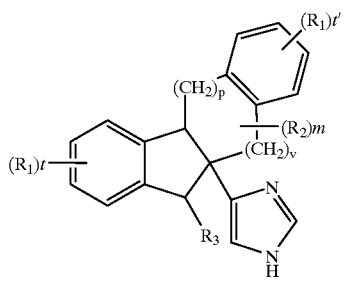

Ib wherein $R_1$, $R_2$, $R_3$ and t are as defined above; m is 0, 1 or 2; t' is 0, 1, 2 or 3; p is 0, 1, 2 or 3; and v is 0, 1, 2 or 3, with the proviso that p+v is 1, 2 or 3.

In a subgroup of compounds Ib, (a) p is 0 and v is 1, 2 or 3, or (b) v is 0 and p is 1, 2 or 3.

A subgroup of compounds Ib are compounds of formula Ib'.

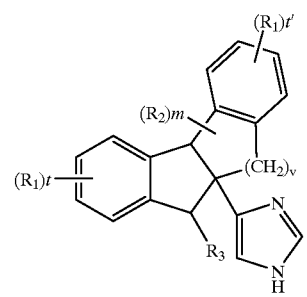

Ib' wherein $R_1$, $R_2$, $R_3$ and t are as defined above; m is 0, 1 or 2; t' is 0, 1, 2 or 3; and v is 1, 2 or 3.

In a subgroup of compounds of formula Ib, m is 0; or m is 1 and $R_2$ is halogen, e.g. F or Cl, or $(C_{1-6})$alkyl; e.g. $(C_{1-6})$alkyl. Preferably, t and/or t' is 0 or 1, e.g. 0. $R_3$ is e.g. H. In one embodiment of the compounds Ib, v is 1 or 2.

The compounds of formula I and the subgroups Ia and Ib, as well as the pharmaceutically acceptable esters and salts thereof, are referred to below as the compounds of the invention, unless otherwise indicated.

The compounds of the invention may have chiral carbon atom(s) in their structure. The invention includes within its scope all the possible stereoisomers of the compounds I, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of, for example, optical isomers, e.g. enantiomers, from the mixture thereof the conventional resolution methods, e.g. fractional crystallisation, may be used.

Physiologically acceptable salts may be prepared by known methods. The pharmaceutically acceptable salts, e.g. acid addition salts, are the usual organic and inorganic salts in the art. Furthermore, the OH- or amino-functionality, when present in the compounds of the invention, can be converted to a pharmaceutically acceptable ester or, respectively, a pharmaceutically acceptable amide with pharmaceutically acceptable acids by known methods. Examples of such pharmaceutically acceptable acids are e.g. aliphatic acids or aromatic acids which are conventional in the field of pharmaceuticals and which retain the pharmacological properties of the free form.

Terms employed herein have the following meanings: A halogen or halo refers to fluorine, chlorine, bromine or iodine. The term $(C_1-C_6)$alkyl as employed herein as such or as part of another group includes both straight, and branched chain radicals of up to 6 carbon atoms, for example of 1, 2, 3 or 4 carbon atoms. The term $(C_1-C_6)$alkoxy as such or as part of another group refers to —$O(C_1-C_6)$alkyl, wherein $(C_1-C_6)$alkyl is as defined above. The term $(C_2-C_6)$alkenyl includes both straight and branched chain radicals of up to 6 carbon atoms, for example of 2, 3 or 4 carbon atoms, containing double bond(s), e.g. one double bond. The term $(C_2-C_6)$alkynyl includes both straight and branched chain radicals of up to 6 carbon atoms, for example of 2, 3 or 4 carbon atoms, containing triple bond(s), e.g. one triple bond. The term halo-$(C_1-C_6)$alkyl refers to $(C_1-C_6)$alkyl radical, as defined above, that is substituted by one or more halo radicals as defined above, e.g. trifluoromethyl, difluoromethyl etc.

The compounds of the invention can be prepared by a variety of synthetic routes analogously or according to the methods known in the literature using suitable starting materials. In general, the compounds of the invention can be prepared e.g. analogously or according to the scheme 1:

Scheme 1

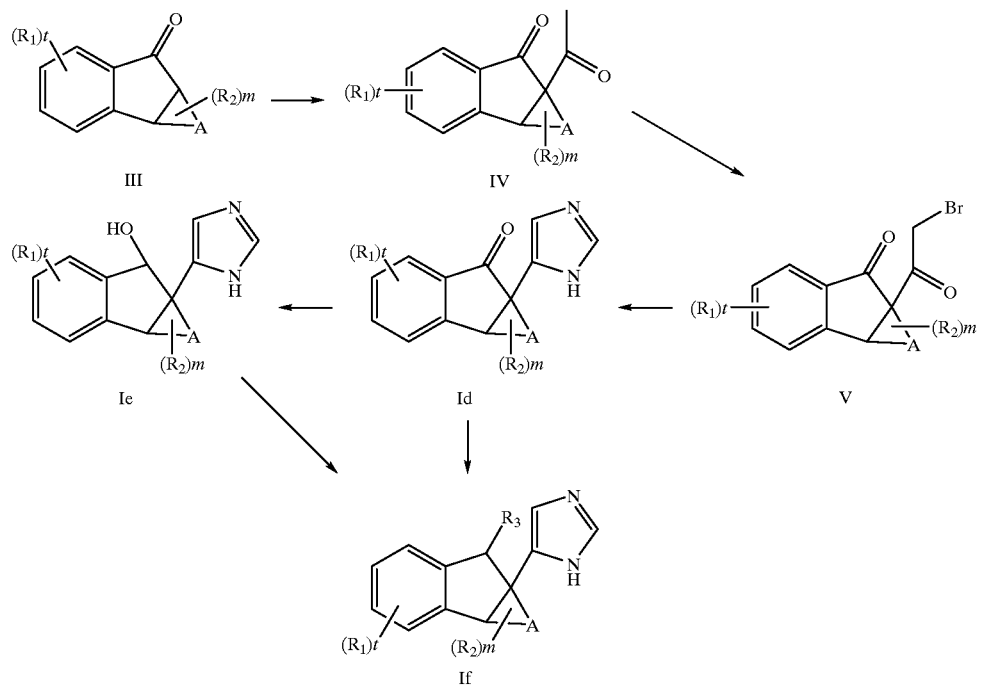

wherein —A— is as defined above except a 3-membered carbocycle; and $R_1$, $R_2$, $R_3$, t and m are as defined above.

According to the reaction route of scheme 1, a compound V is formed either by reacting a compound III with acetic anhydride to obtain a compound IV (see V. E. Dehmlow et al., Liebigs Ann. Chem., 1977, p.1617–1624, or R. M. Manyik et al., J. Am. Chem. Soc., vol.75, 1953, p.5030–5032), which is then reacted with $Br_2$ in a suitable solvent, e.g. methanol. The compound V thus obtained is reacted with formamide to form an end compound I, wherein $R_3$ is =O (compound Id). The said =O as $R_3$ in the compound Id can then further be converted to another $R_3$ of the invention in a manner known in the art. For example, it can be reduced in a suitable solvent to a compound Ie using suitable reducing agent, e.g. $NaBH_4$ or it can be reduced e.g. with $H_2NNH_2$ to a compound If, wherein $R_3$ is H (see B. C. Ranu and U. Jana, J. Org. Chem., vol.64, 1999, p.6380–6386). Also the OH-group of the compound Ie can further be converted to another functionality $R_3$ of the invention. The above steps can be carried out at room or elevated temperature in a manner known in the art.

Scheme 2 illustrates an alternative route for preparing compounds I:

Scheme 2

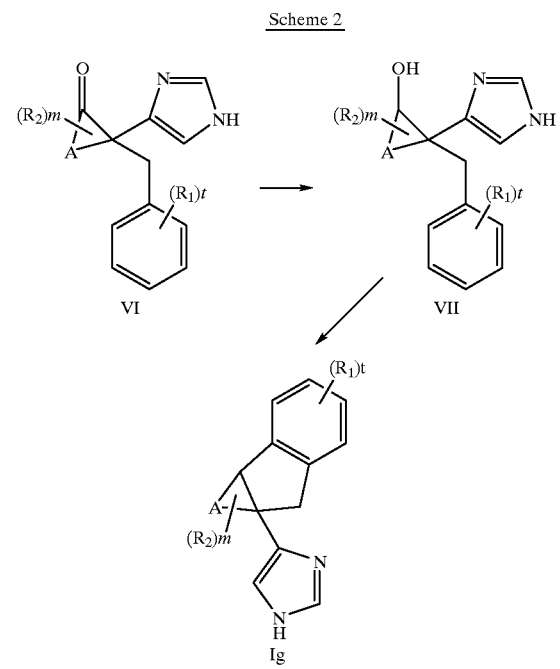

wherein $R_1$, $R_2$, m and t are as defined above and —A— is as defined above except 3- or 4-membered carbocycle.

Accordingly, a starting compound VI is reduced with a suitable reducing agent, e.g. $NaBH_4$, in a conventional manner, in a suitable solvent, e.g. ethanol, to a corresponding alcohol VII, which is then cyclized in a known manner to the end compound Ig using a strong acid, e.g. $MeSO_3H$.

A further alternative route for preparing compounds of formula 1, wherein —A— forms a fused saturated monocyclic carbocycle of 5 ring atoms (i.e. cyclopenta), is illustrated in scheme 3:

titanium(0) (produced in situ). The carbonyl group of the compounds of formula I' can, if desired, further be reduced in a conventional manner to obtain a corresponding alcohol compound Ih of the invention. An optional well known elimination of water from the said alcohol compound Ih results in compounds of formula Ii. The double bond can further be hydrogenated in a usual manner to obtain a corresponding saturated compound Ij. The above-mentioned ketone or alcohol functionality can also be converted with

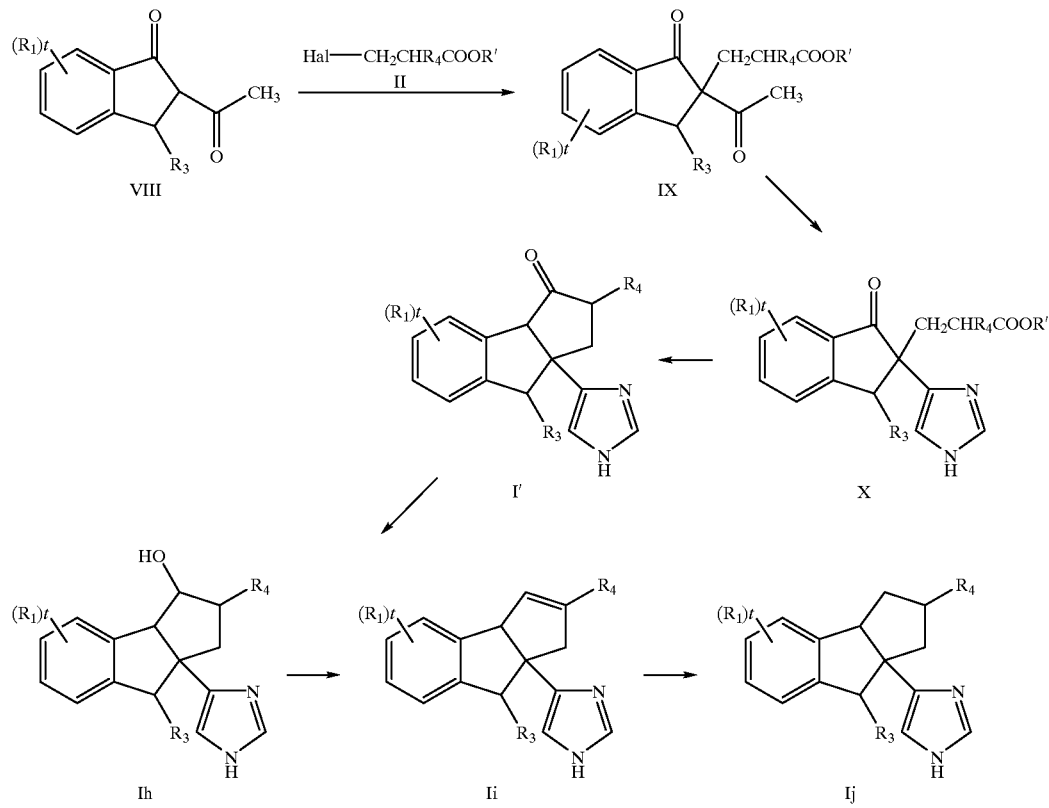

Scheme 3 wherein $R_1$, $R_3$ and t are as defined above, $R_4$ is H or $(C_{1-6})$alkyl, Hal is a halogen, e.g. Br, and R' is a $(C_{1-6})$alkyl, e.g. ethyl Accordingly, a compound VII is reacted with a compound II in the presence of a base, e.g. potassium carbonate, to form an ester IX, which is reacted first with bromine and then with formamide to form compound X. The resulted compound X is cyclized according to McMurry reaction in a suitable solvent, e.g. THF, in the presence of a catalyst, e.g.

another suitable alternative given for $R_2$ in a manner known in the art. Each of the above reactions can be carried out in a suitable reaction temperature, e.g., at room or elevated temperature.

A further alternative route for preparing compounds of formula I, wherein —A— forms a fused, partially or fully saturated monocyclic carbocycle of 3 ring atoms (i.e., cyclopropa ring); and m is 0, is illustrated in scheme 4:

Scheme 4

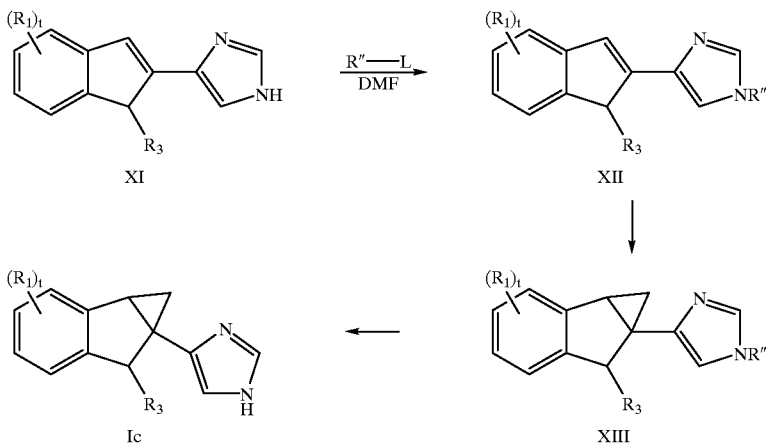

wherein $R_1$, $R_3$ and t are as defined above; and R" is a conventional protecting group for =NH in the imidazole ring, e.g., benzyl, —$CPh_3$ (trityl) or $SO_2NMe_2$.

Accordingly, =NH of the imidazole moiety of a compound XI is protected in a conventional manner. The resulted compound XII can be converted to a corresponding cyclopropa-fused compound XIII analogously to e.g. the Simmons-Smith procedure using $ZnEt_2$ in a suitable solvent, e.g. $CH_2Cl_2$ (see e.g. P. T. Kaye is and W. E. Molema, Synt. Commun., vol.29(11), 1999, p.1889–1902). The compound XIII is finally deprotected in a conventional manner to obtain the end compound Ic. Each of the above reactions are carried out in a suitable reaction temperature, e.g. at room or elevated temperature.

Generally, if applicable, a substituent as $R_1$, $R_2$ and/or $R_3$ in a compound of formula I prepared according to the above reaction schemes can be converted in a conventional manner to another substituent of the invention.

The starting materials of formulae III, VI, VIII and XI are commercially available or can be prepared via a variety of known synthetic routes known in the literature.

For example the starting material of formula III for the synthetic route of scheme 1 can be e.g. prepared analogously or according to scheme 5a:

Scheme 5a

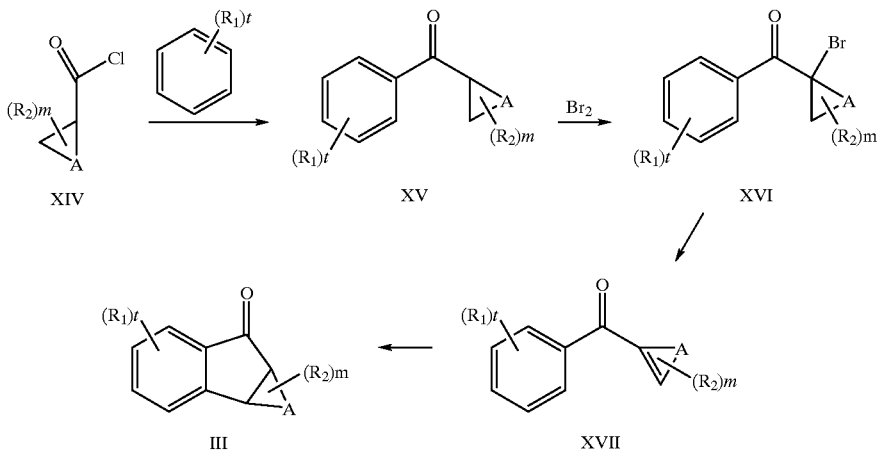

wherein —A— is as defined above except 3- or 4-membered carbocycle; and $R_1$, $R_2$, m and t are as defined above.

Accordingly, a compound XIV is reacted with an optionally $(R_1)_t$-substituted benzene in a suitable solvent, e.g. dichloromethane, analogously to the Friedel-Crafts acylation procedure to obtain a compound XV. The compound XV is then reacted in a suitable solvent, e.g. dichlormethane, with bromine in acidic reaction conditions, whereby compound XVII is formed, which is then cyclized in a known manner in the presence of a strong acid, e.g. $H_2SO_4$, to obtain a starting compound III (see e.g. H. O. House et al., J. Am. Chem. Soc., vol.82, 1960, p.1457–1462). Each of the above reactions are carried out in a suitable reaction temperature, e.g. at room or elevated temperature.

A further route for preparing starting compounds of formula III is illustrated in scheme 5b:

Scheme 5b

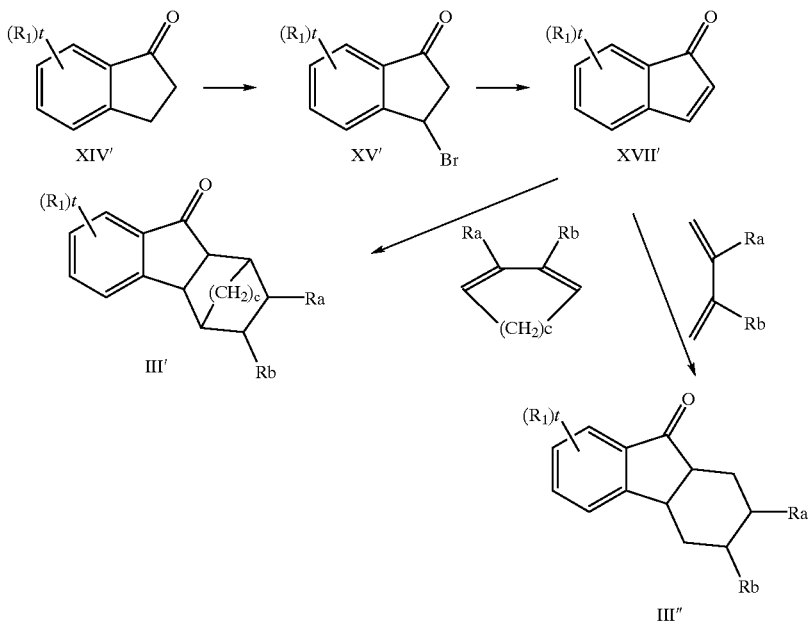

wherein $R_1$ and t are as defined above, Ra and Rb are independently H or as defined for $R_2$ above, and c is 1 or 2.

Accordingly, compound XIV' is reacted via a bromine derivative XV' to a compound XVII', e.g., analogously to a procedure described by P. E. Hansen and K. Undheim in Acta Chem.Scand., vol.27(3), 1973, p.1112–1113. The compound XVII' is then reacted with a diene derivative analogously to a known Diels-Alder procedure (cf. e.g. S. Gosh and S. Saha, Tetrahedron, vol.41, 1985, p.349–355). The above reaction steps are carried out in suitable temperatures and solvents obvious for a skilled person.

The starting compound of formula VI for the synthetic route of scheme 2 can be, for example, prepared analogously or according to scheme 6:

Scheme 6

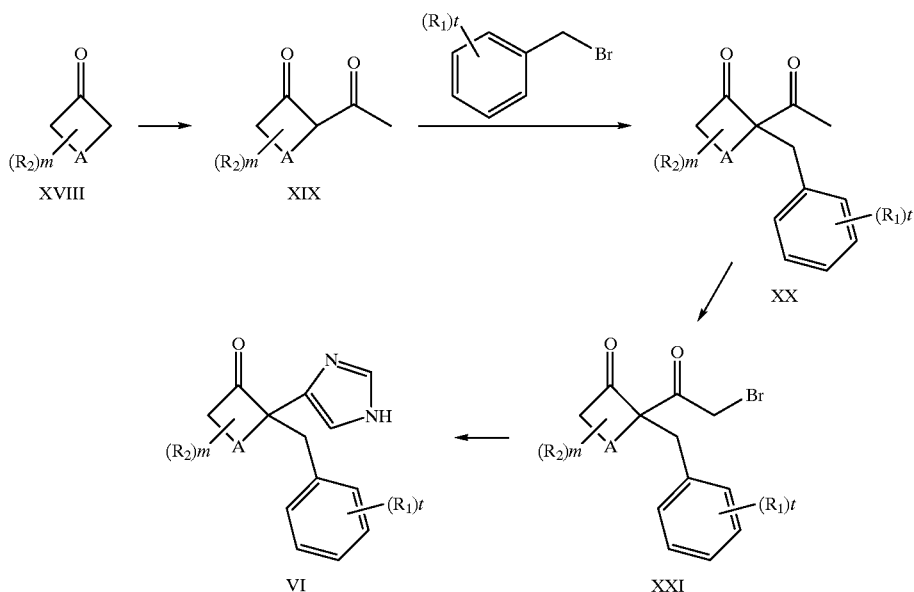

wherein $R_1$, $R_2$, m and t are as defined above and —A— is as defined above except 3- or 4-membered carbocycle.

Accordingly, a compound XVIII is acylated in acidic conditions to obtain a compound XIX which is then reacted with a benzyl bromide derivative in the presence of a base, e.g. potassium carbonate, in a suitable solvent. The resulted compound XX is reacted with bromine in a suitable solvent, e.g. methanol. The compound XXI thus obtained is allowed to react with formamide to form a starting compound VI. Each of the above reactions are carried out in a suitable reaction temperature, e.g., at room or elevated temperature.

The starting material for the synthetic route of scheme 3 (e.g., compound VIII) and also the starting material for the synthetic route of scheme 4 (e.g., compound XI) can be e.g. prepared analogously or according to the methods described in EP-A-0 183 492, the contents of which are hereby incorporated by reference.

Furthermore, the starting materials for preparing the above compounds III, VI, VIII, XI, XIV' and the diene derivatives described in scheme 5b are commercially available or can be prepared analogously or according to the methods described in the literature (see the above cited EP-A-0 183 492).

It is obvious to a skilled person that, in the above reactions, any starting material or intermediate can be protected, if necessary, in a manner well known in the chemical field. Any protected functionality is subsequently deprotected in a usual manner.

The above described synthetic routes are meant to illustrate the preparation of the compounds of the invention and the preparation is by no means limited thereto, i.e., other synthetic methods that are within the general knowledge of a skilled person are also possible.

The compounds of the invention may be converted, if desired, into their pharmaceutically acceptable salt or ester form using methods well known in the art.

The compounds of the invention show interesting pharmacological properties, namely they exhibit affinity for alpha2 adrenoceptors. This activity is demonstrated in the pharmacological tests presented below.

EXPERIMENT I

Antagonist Activity on Alpha2 Adrenoceptors (alpha2AR) in Rat Vas Deferens in Vitro Rats were killed by $CO_2$-suffocation. Vas deferentia were dissected out and both prostatic halves were removed to tissue chambers containing Krebs-solution of the following composition (mM): NaCl 118, KCl 4.7, $CaCl_2$ 2.5, $KH_2PO_4$ 1.2, $MgSO_4$ 0.6, $NaHCO_3$ 25, glucose 11.1, aerated by 5% carbogen, temperature 37° C., pH 7.4. Propranolol 260 g/l and desipramine 2 g/ml were added to prevent the possible effects on alpha-adrenergic receptors and to prevent re-uptake of released norepinephrine, respectively. Preparations were tied to the bottom hooks of the incubation chambers and the to isometric force-displacement transducers above. Electrical stimulation was started after the equilibrium period/5 minutes under a resting tension of 0.5 g) by introducing field stimulation with the following parameters: twin-pulses, voltage 70 V, frequency 0.2 Hz, delay 5 ms, duration 2 ms. As soon as the electrically induced twitch response was stabilised, the test compounds were administered by a cumulative fashion with half logarithmic increments at five minutes intervals. Inhibition of the electrically evoked contractions was measured as the response to alpha2AR agonists. Antagonist was administered into the incubation medium at least five minutes before agonist. Means±SEM of percentage inhibition were calculated in the absence and in the presence of antagonist and expressed as dose-response curves. In order to express the antagonist potency, pA2-value was calculated. The results of the test are reported in table 1.

TABLE 1

| Compound of example No. | Vas deferens Alpha2 antagonistic activity |
| --- | --- |
| Example 1(e) | pA2 = 8.4 |
| Exampfe 2(a) | pA2 = 7.8 |
| Example 2(b) | pA2 = 7.4 |
| Exampje 3(i) | pA2 = 8.2 |
| Example 4 | pA2 = 7.4 |
| Example 5(a) | pA2 = 6.9 |
| Example 5(b) | pA2 = 7.7 |
| Example 6 | pA2 = 6.0 |
| Example 7(f) | pA2 = 5.3 |
| Example 8 | pA2 = 7.4 |

In general, the compounds of the invention exhibiting alpha2-antagonistic activity may be useful for therapeutical indications in which alpha2-antagonists are used. They may also be used for reversal of the effects of alpha2-agonists.

Accordingly, the compounds of the invention may be useful, for example, in the treatment of different neurological, psychiatric and cognition disorders. Furthermore, they may be used in the treatment of various peripheral disorders, e.g. diabetes, orthostatic hypotension, lipolytic disorders (such as obesity) or sexual dysfunction.

The compounds of the invention may be administered enterally, topically or parenterally.

The compounds of the invention may be formulated alone or together with another active ingredient and/or together with a pharmaceutically acceptable diluent, carrier and/or excipient in different pharmaceutical unit dosage forms, e.g. tablets, capsules, solutions, emulsions and powders etc., depending on the route of administration, using conventional techniques. The pharmaceutically acceptable diluent, carrier and/or excipient can be selected from those conventionally used in the field of pharmaceuticals noticing the chosen route of administration.

The amount of the active ingredient varies from 0.01 to 75 weight-% depending on i.a. the type of the dosage form.

The specific dose level of the compounds of the invention depends on several factors such as the compound to be administered, the species, age and the sex of the subject to be treated, the condition to be treated and on the route and method of administration. Accordingly, the dosage for parenteral administration is typically from 0.5 µg/kg to 10 mg/kg per day and that for oral administration is typically from 5 µg/kg to 100 mg/kg for an adult male.

The present invention also provides a compound of the invention or an ester or salt thereof for use in a method of treatment of human or animal body.

The present invention further provides a compound of the invention or an ester or salt thereof for use as alpha-2 antagonist, i.a. in the treatment of diseases and conditions where alpha-2 antagonists are indicated to be used, e.g. in the treatment of above indicated diseases and conditions. The use of the compounds of the invention for the manufacture of a medicament to be used for the above indications is also provided. The invention further relates to a method for the treatment of above indicated conditions or diseases, by administering to a subject in need of such treatment an effective amount of the compound of the invention or a pharmaceutically acceptable ester or salt thereof.

The present invention will be explained in more detail by the following examples. The examples are meant only for illustrating purposes and do not limit the scope of the invention defined in claims.

EXAMPLE 1 a) 3-(2-Acetyl-1-oxoindan-2-yl)propionic Acid Ethyl Ester

2-Acetyl-1-indanone (15 g, cf. Liebigs Ann. Chem. 347 (1906) 112) was added into a mixture of potassium carbonate (8.5 g) and dry N,N-dimethylformamide (45 ml). The mixture was stirred at 50–55° C. for 20 minutes and ethyl 3-bromopropionate (19 g) was then added and the stirring was continued at 50–55° C. for 6 hours. Water (60 ml) was added to the reaction mixture and the pH of the solution was adjusted to 2–3 with hydrochloric acid. The mixture was stirred at 50–55° C. for one hour. The cooled solution was extracted with toluene, washed with water, dried with sodium sulfate, and the solvent removed under reduced pressure. The yield was 23.5 g.

$^1$H NMR (CDCl$_3$): 1.23 (3H, t, J=7.1 Hz), 2.26 (3H, s), 2.22–2.48 (4H, m), 2.91 (1H, d, J=17.4 Hz), 3.82 (1H, d, J=17.4 Hz), 4.11 (2H, q, J=7.1 Hz), 7.39 (1H, t), 7.50 (1H, d), 7.63 (1H, t), 7.74 (1H, d).

b) 3-[2-(1H-Imidazol-4-yl)-1-oxoindan-2-yl]propionic Acid Ethyl Ester 3-(2-Acetyl-1-oxoindan-2-yl)propionic acid ethyl ester (20.0 g) was dissolved in 100 ml of methylene chloride and 4.5 ml of bromine was slowly added at 20–25° C. The reaction mixture was stirred at 20–25° C. for 4 hours after that it was washed with diluted sodium bicarbonate solution and water. The organic phase was dried with sodium sulfate and the solvent was removed under reduced pressure. Formamide (110 ml) was added into the residue and the mixture was heated at 130–140° C. for 6 hours. The reaction mixture was poured into water (150 ml) and acidified with hydrochloric acid. The acidic solution was washed with methylene chloride and the aqueous phase was basified with sodium hydroxide solution. The product was extracted into methylene chloride which thereafter was washed with water, dried with sodium sulfate and the solvent removed under reduced pressure. The crude product was purified by flash chromatography using methanol/methylene chloride (1:100) as eluent. The yield was 4.0 g, m.p. 162–165° C.

$^1$H NMR (CDCl$_3$): 1.19 (3H, t, J=7.1 Hz), 2.17–2.39 (4H, m), 3.30 (1H, d, J=17.3 Hz), 3.81 (1H, d, J=17.3 Hz), 4.06 (2H, q, J=7.1 Hz), 6.98 (1H, s), 7.37 (1H, t), 7.48 (1H, d), 7.53 (1H, s), 7.61 (1H, t), 7.75 (1H, d).

(c) 8a-(1H-Imidazol-4-yl)-1,3a,8,8a-tetrahydro-2H-cyclopenta[a]inden-3-one

Titanium tetrachloride (5.5 ml) was added dropwise to a stirred suspension of zinc powder (6.5 g) in dry tetrahydrofuran (300 ml) with ice cooling under a nitrogen atmosphere. The mixture was heated at reflux for one hour. 3-[2-(1H-Imidazol-4-yl)-1-oxoindan-2-yl]propionic acid ethyl ester (3.0 g) in 100 ml of dry tetrahydrofuran was then added to the refluxing mixture during 4 hours. After a further 2 hour reflux period, the reaction mixture was cooled to room temperature, quenched by cautious addition of 30 ml of methanol and the pH of the mixture was adjusted to 8–9 with aqueous sodium hydroxide solution. The slurry was filtered and the filtrate was evaporated to dryness under reduced pressure. The residue was stirred in aqueous hydrochloric acid at room temperature for 2 hours. Work-up of the reaction mixture gave the crude product, which was purified by flash chromatography using methylene chloride/methanol (97:3) as eluent. The yield was 1.2 g, m.p. 234–236° C.

$^1$H NMR (MeOH-d4): 2.01–2.08 (1H, m), 2.22–2.34 (1H, m), 2.37–2.55 (2H, m), 3.26 (1H, d, J=16.2 Hz), 3.39 (1H, d, J=16.2 Hz), 3.98 (1H, s), 7.01 (1H, s), 7.16–7.35 (4H, m), 7.67 (1H, s).

d) 8a-(1H-Imidazol-4-yl)-1,2,3,3a,8,8a-hexahydrocyclopenta[a]inden-3-ol

To a solution of 8a-(1H-imidazol-4-yl)-1,3a,8,8a-tetrahydro-2H-cyclopenta[a]inden-3-one (1 g) in 40 ml of ethanol was added 0.16 g of sodium borohydride under a nitrogen atmosphere. The reaction mixture was stirred at 35–40° C. for 4 hours and then poured into water (100 ml) and extracted with methylene chloride (3×100 ml). The combined organic layers were dried over sodium sulfate and the solvent removed under reduced pressure. The crude product was purified by flash chromatography using methylene chloride/methanol (95:5) as eluent. The yield was 0.6 g, m.p. 183–186° C.

$^1$H NMR (CDCl$_3$): 1.64–1.72 (1H, m), 2.02–2.21 (3H, m), 3.23 (1H, d, J=16.9 Hz), 3.41 (1H, d, J=16.9 Hz), 3.80 (1H, d, J=7.3 Hz), 4.51–4.57 (1H, m), 6.76 (1H, s), 7.21–7.30 (4H, m), 7.52 (1H, s).

e) 4-(2,3,3a,8-Tetrahydro-1H-cyclopenta[a]inden-8a-yl)-1H-imidazole

A solution of 8a-(1H-imidazol-4-yl)-1,2,3,3a,8,8a-hexahydrocyclo-penta[a]inden-3-ol (0.5 g) in 20 ml of ethanol containing 5 ml of 20% hydrochloric acid was heated at reflux for 3 hours. The solution was allowed to cool to room temperature and 50 mg of 10% palladium on carbon catalyst was added. The reaction mixture was hydrogenated at 50–55° C. until no more hydrogen was consumed. The catalyst was filtered off and the solvent removed under reduced pressure. The residue was dissolved in water and the solution was basified with sodium hydroxide solution. The basic reaction solution was extracted with methylene chloride (3×100 ml), dried over sodium sulfate and the solvent was removed under reduced pressure. The crude product was purified by flash chromatography using methylene chloride/methanol (97:3) as eluent. Recrystallization from ethyl acetate afforded 120 mg of product, m.p. 171–174° C.

$^1$H NMR (CDCl$_3$): 1.55–1.91 (4H, m), 2.11–2.26 (2H, m), 3.19 (1H, d, J=16.5 Hz), 3.37 (1H, d, J=16.5 Hz), 3.75 (1H, m), 6.82 (1H, s), 7.16–7.26 (4H, m), 7.55 (1H, s).

EXAMPLE 2 a) 4-(3-Methylene-2,3,3a,8-tetrahydro-1H-cyclopenta[a]inden-8a-yl)-1H-imidazole

A mixture of potassium tert-butoxide (0.38 g) and methyltriphenyl-phosphonium bromide (1.2 g) in dry toluene (20 ml) was heated at reflux for 0.5 hour. To the mixture was then added 0.55 g of 8a-(1H-imidazol-4-yl)-1,3a,8,8a-tetrahydro-2H-cyclo-penta[a]inden-3-one and the resulting mixture was heated at reflux for 4 hours. After the removal of toluene, the residue was suspended in water and extracted with methylene chloride. The combined organic layers were dried over sodium sulfate and the solvent removed under reduced pressure. The crude product was purified by flash chromatography using methylene chloride/methanol (95:5) as eluent. Recrystallization from ethyl acetate afforded 240 mg of the product, m.p. 167–174° C.

$^1$H NMR (CDCl$_3$): 1.86–1.97 (1H, m), 2.16–2.24 (1H, m), 2.42–2.53 (2H, m), 3.23 (1H, d, J=16.2 Hz), 3.35 (1H, d, J=16.2 Hz), 4.13 (1H, s), 5.02 (1H, s), 5.20 (1H, s), 6.85 (1H, s), 7.19–7.32 (4H, m), 7.59 (1H, s).

b) 4-(3-Methyl-2,3,3a,8-tetrahydro-1H-cyclopenta[a]inden-8a-yl)-1H-imidazole 4-(3-Methylene-2,3,3a,8-tetrahydro-1H-cyclopenta[a]inden-8a-yl)-1H-imidazole (0.23 g) was dissolved in 20 ml of ethanol and the mixture was hydrogenated at 50–55° C. with 10% palladium on carbon as catalyst until no more hydrogen was consumed. The catalyst was filtered off and the solvent removed under reduced pressure. The residue was crystallized from ethyl acetate. The yield was 0.14 g, m.p. 168–172° C.

$^1$H NMR (CDCl$_3$): 0.92 (3H, d, J=7.0 Hz), 1.21–1.36 (1H, m), 1.81–1.90 (1H, m), 1.98–2.05 (1H, m), 2.10–2.20 (1H, m), 2.40–2.52 (1H, m), 3.13 (1H, d, J=16.8 Hz), 3.33 (1H, d, J=16.8 Hz), 3.62 (1H, d, J=9.3 Hz), 6.78 (1H, s), 7.11–7.26 (4H, m) 7.50 (1H, s).

EXAMPLE 3 a) Cyclohexylphenyl Ketone

A solution of cyclohexanecarbonyl chloride (9.1 ml) in $CH_2Cl_2$ (25 ml) was added slowly under nitrogen atmosphere at 0–4° C. to a stirred mixture of $AlCl_3$ (9.1 g), $CH_2Cl_2$ (25 ml) and benzene (50 ml). The resulting mixture was stirred for 1 hour at 0–4° C. and 12 hours at the room temperature. The mixture was poured into ice-water (200 ml, contains 1 ml of concentrated HCl) and stirred for 5 minutes. The phases were separated and the aqueous phase was washed with $CH_2CO_2$ (2×20 ml). The organic phases were combined and extracted with water (2×20 ml), 2.5% NaOH solution (2×30 ml) and water (2×20 ml). The organic phase was dried over $Na_2SO_4$ and evaporated. Yield was 12.0 g.

$^1$H NMR ($d_6$-DMSO): 1.10–1.45 (6H, m), 1.60–1.81 (4H, m), 3.39 (1H, m), 7.49 (2H, m), 7.62 (1H, m), 7.95 (2H, m).

b) (1-Bromocyclohexyl)phenyl Ketone

Temperature was kept at 20–25° C. when bromine (2.8 ml) was added slowly to a stirred mixture of cyclohexylphenyl ketone (10 g) in $CH_2Cl_2$ (50 ml) and acetic acid (1 ml). The mixture was stirred at the ambient temperature for 1 hour and extracted with 5% $NaHCO_3$ (2×30 ml) and water (30 ml). The organic phase was dried over $Na_2SO_4$ and evaporated. Yield was 14.1 g.

$^1$H NMR ($d_6$-DMSO): 1.30–1.71 (6H, m), 2.15–2.28 (4H, m), 7.51 (2H, m), 7.58 (1H, m), 7.96 (2H, m).

c) Cyclohex-1-enylphenyl Ketone (1-Bromocyclohexyl)phenyl ketone (14.1 g) was dissolved in pyridine (60 ml) and the mixture was refluxed for 1 hour. After cooling to the ambient temperature the mixture was filtered and evaporated. The residue was dissolved in $CH_2Cl_2$ (50 ml) and extracted with 1 M HCl (2×30 ml) and water (30 ml). The organic layer was dried over $Na_2SO_4$ and evaporated. Yield was 9.7 g.

$^1$H NMR ($d_6$-DMSO): 1.64 (4H, m), 2.27 (4H, m), 6.52 (1H, m), 7.47 (2H, m), 7.57 (3H, m).

d) 1,2,3,4,4a,9a-Hexahydrofluoren-9-one

Cyclohex-1-enylphenyl ketone (9.7 g) was slowly added to a concentrated $H_2SO_4$ solution (100 ml) at room temperature and the resulting mixture was placed into a preheated oil bath (110° C.) for 20 minutes. The hot mixture was poured into ice-water (400 ml) and extracted with $CH_2Cl_2$ (4×40 ml). The organic phase was washed with 5% NaHCO3 solution (2×30 ml) and water (30 ml). After drying over $Na_2SO_4$ and evaporation the yield was 9.6 g.

$^1$H NMR ($d_6$-DMSO): 1.03 (2H, m), 1.37 (2H, m), 1.51 (1H, m), 1.68 (1H, m), 1.95 (1H, m), 2.11 (1H, m), 2.79 (1H, m), 3.40 (1H, m), 7.42 (1H, m), 7.60 (1H, m), 7.66 (2H, m).

e) 9a-Acetyl-1,2,3,4,4a,9a-hexahydrofluoren-9-one 1,2,3,4,4a,9a-Hexahydrofluoren-9-one (9.6 g) was dissolved in acetic anhydride (40 ml). p-Toluenesulfonic acid (1 g) was added and the mixture was refluxed for 1 hour. The mixture was cooled in an ice bath and water (20 ml) was added. After stirring for 20 minutes solvent was removed with an evaporator. The residue was dissolved in ethyl acetate (60 ml) and extracted with 5% $NaHCO_3$ solution (2×30 ml) and water (30 ml). The organic phase was dried over $Na_2SO_4$ and evaporated. Yield was 10.9 g.

$^1$H NMR ($d_6$-DMSO): 1.19 (2H, m), 1.41 (2H, m), 1.68 (1H, m), 1.79 (1H, m), 2.01 (2H, m), 2.15 (3H, s), 3.89 (1H, t, J=6.1 Hz), 7.47 (1H, m), 7.68 (2H, m), 7.74 (1H, m).

f) 9a-(2-Bromoacetyl)-1,2,3,4,4a,9a-hexahydrofluoren-9-one

Bromine (1.2 ml) was added to a mixture of 9a-acetyl-1,2,3,4,4a,9a-hexahydrofluoren-9-one (5 g) in methanol (20 ml) at 20–30° C. The reaction mixture was stirred for 2 hours and quenched with $NaHCO_3$ solution (0.8 g $NaHCO_3$ and 24 ml water). The mixture was extracted with $CH_2Cl_2$ (3×30 ml) and the organic phase was washed with water (30 ml) and dried over $Na_2SO_4$. Evaporation gave 6.6 g of the crude product which was used without further purification for the next step.

$^1$H NMR ($d_6$-DMSO): 1.10–1.55 (4H, m), 1.66 (1H, m), 1.90 (1H, m), 1.97 (1H, m), 2.17 (1H, m), 3.97 (1H, t, J=5.6 Hz), 4.65 (2H, m), 7.48 (1H, m), 7.69 (2H, m), 7.75 (1H, m).

g) 9a-(1H-Imidazol-4-yl)-1,2,3,4,4a,9a-hexahydrofluoren-9-one 9a-(2-Bromoacetyl)-1,2,3,4,4a,9a-hexahydrofluoren-9-one (6.6 g) was mixed with formamide (22 ml) and the mixture was heated at 135° C. for 30 minutes. Ammonia gas was led into the reaction mixture and the stirring was continued at 135° C. for further 4 hours. After cooling to the ambient temperature the mixture was diluted with $CH_2Cl_2$ (30 ml) and water (30 ml). The phases were separated and the aqueous phase was extracted with $CH_2Cl_2$ (30 ml). The combined organic phases were mixed with water (60 ml) and the pH was adjusted to 1 with concentrated HCl solution. The layers were separated and the aqueous phase was washed with $CH_2Cl_2$ (30 ml). The aqueous phase was mixed with $CH_2Cl_2$ (60 ml) and the pH was adjusted to 11.5–13.5 with 48% NaOH solution. The phases were separated and the aqueous phase was extracted with $CH_2Cl_2$ (20 ml). The combined organic phases were washed with water (50 ml), dried over $Na_2SO_4$ and evaporated. The yield was 2.2 g.

$^1$H NMR ($d_6$-DMSO): 1.16 (1H, m), 1.33 (1H, m), 1.46 (2H, m), 1.62 (1H, m), 1.91 (2H, m), 2.01 (1H, m), 3.98 (1H, t, J=5.4 Hz), 7.02 (1H, s), 7.43 (1H, m), 7.51 (1H, s) 7.64 (2H, m), 7.70 (1H, m).

h) 9a-(1H-Imidazol-4-yl)-2,3,4,4a,9,9a-hexahydro-1H-fluoren-9-ol 9a-(1H-Imidazol-4-yl)-1,2,3,4,4a,9a-hexahydrofluoren-9-one (0.41 g) was dissolved in ethanol (10 ml). 48% NaOH solution (0.003 ml) and $NaBH_4$ (0.06 g) was added and the mixture was heated at 40° C. for 12 hours. Water (2.5 ml) was added and the mixture was cooled to the ambient temperature. HCl (0.3 ml of 30% HCl in 1 ml $H_2O$) was added and the mixture was stirred for 5 minutes. NaOH (0.2 ml of 48% NaOH in 5 ml $H_2O$) was then added and the solvents were evaporated. The residue was mixed with water (30 ml) and extracted with $CH_2Cl_2$ (3×30 ml) and evaporated. The crude product was purified by flash chromatography using methylene chloride/methanol (95:5) as eluent. The yield was 0.26 g.

$^1$H NMR ($d_6$-DMSO): 1.17 (3H, m), 1.49 (3H, m), 1.94 (1H, m), 2.23 (1H, m), 3.61 (1H, bs), 4.95 (1H, s), 7.27 (4H, m), 7.71 (1H, s), 9.13 (1H, s) 14.43 (1H, bs), i) 4-(4b,5,6,7,8,9-Hexahydrofluoren-8a-yl)-1H-imidazole 9a-(1H-Imidazol-4-yl)-1,2,3,4,4a,9a-hexahydrofluoren-9-one (2.5 g) was mixed with di(ethylene glycol) (50 ml), hydrazine hydrate (7.2 ml) and KOH (9.5 g). The mixture was heated at 150° C. for 30 minutes and at 190° C. for 4 hours. After cooling to the ambient temperature the reaction mixture was diluted with water (150 ml) and extracted with $CH_2Cl_2$ (4×50 ml). The organic phase was washed with water (30 ml). The organic phase was mixed with water (200 ml) and the pH was adjusted to 1 with concentrated HCl solution. The layers were separated and the aqueous phase was washed with $CH_2Cl_2$ (2×30 ml). The aqueous phase was mixed with $CH_2Cl_2$ (150 ml) and the pH was adjusted to 11.5–13.5 with 48% NaOH solution. The phases were separated and the aqueous phase was extracted with $CH_2Cl_2$ (2×30 ml). The combined organic phases were washed with water (50 ml), dried over $Na_2SO_4$ and evaporated. The yield was 1.4 g.

$^1$H NMR ($d_6$-DMSO): 1.25–1.59 (5H, m), 1.89 (1H, m), 1.94 (1H, m), 2.09 (1H, m), 2.90 (1H, d, J=15.2 Hz), 3.05 (1H, d, J=15.2 Hz), 3.58 (1H, t, J=4.2 Hz), 6.93 (1H, d, J=1.1 Hz), 7.19 (4H, m), 7.62 (1H, d, J=1.1 Hz), 14.35 (1H, bs).

EXAMPLE 4

4-(3-Fluoro-4b,5,6,7,8,9-hexahydrofluoren-8a-yl)-1H-imidazole 9a-(1H-Imidazol-4-yl)-2,3,4,4a,9,9a-hexahydro-1H-fluoren-9-ol was synthesised according to the procedure described in example 4. Fluorobenzene was used as a starting material. 9a-(1H-Imidazol-4-yl)-2,3,4,4a,9,9a-hexahydro-1H-fluoren-9-ol (0.53 g) was dissolved in $CH_2Cl_2$ (20 ml). Triethyl silane (2.5 ml) and trifluoro acetic acid (4.8 ml) was added and the mixture was refluxed for 20 hours. Solvent was evaporated and the residue was mixed with $CH_2Cl_2$ (30 ml) and water (40 ml). The pH was adjusted to 11.5–13.5 with 48% NaOH solution. The phases were separated and the aqueous phase was extracted with $CH_2Cl_2$ (2×20 ml). The combined organic phases were washed with water (20 ml), dried over $Na_2SO_4$ and evaporated. The yield was 0.47 g.

$^1$H NMR ($d_6$-DMSO): 1.17 (2H, m), 1.43 (3H, m), 1.73 (1H, m), 1.91 (1H, m), 2.10 (1H, m), 2.93 (2H, s), 3.58 (1H, bs), 6.98 (1H, td, J=8.2 Hz and 2.3 Hz), 7.13 (1H, dd, J=9.5 and 2.3 Hz), 7.28 (1H, dd, J=8.2 and 5.4), 7.69 (1H, d, J=9.12 (1H, d, J=1.2 Hz) 14.25 (1H, bs).

EXAMPLE 5 a) 4-(3-Methoxy-4b,5,6,7,8,9-hexahydrofluoren-8a-yl)-1H-imidazole 4-(3-Methoxy-4b,5,6,7,8,9-hexahydrofluoren-8a-yl)-1H-imidazole was synthesised according to the procedure described in example 4. Anisole was used as a starting material.

$^1$H NMR ($CDCl_3$): 1.20–2.10 (8H, m), 2.85 (1H, d, J=14.7 Hz), 2.97 (1H, d, J=14.7 Hz), 3.53 (1H, bs), 3.81 (3H, s), 6.70 (1H, dd, J=8.2 Hz and 2.5 Hz), 6.76 (1H, d, J=2.5 Hz), 6.92 (1H, d, J=1.0 Hz), 7.11 (1H, d, J=8.2), 7.60 (1H, d, J=1.0 Hz).

b) 8a-(1H-Imidazol-4-yl)-5,6,7,8,8a,9-hexahydro-4bH-fluoren-3-ol 4-(3-Methoxy-4b,5,6,7,8,9-hexahydrofluoren-8a-yl)-1H-imidazole (0.042 g) was mixed with 48% HBr (2 ml) and refluxed for 2 hours. After cooling to the ambient temperature, water (2 ml) was added and the pH was adjusted to 10 with 25% $NH_3$-solution. The precipitated crude product was filtered and washed with water (10 ml). Recrystallisation from methylene chloride/methanol (95:5) gave the pure product. The yield was 0.030 g.

$^1$H NMR ($CDCl_3$/$d_6$-DMSO): 1.20–1.58 (5H, m), 1.79 (1H, m), 1.94 (1H, m), 2.03 (1H, m), 2.76 (1H, d, J=14.7 Hz), 2.95 (1H, d, J=14.7 Hz), 3.53 (1H, bs), 6.63 (1H, dd, J=8.0 Hz and 2.3 Hz), 6.69 (1H, d, J=2.3 Hz), 6.89 (1H, d, J=1.0 Hz), 6.99 (1H, d, J=8.0), 7.62 (1H, d, J=1.0 Hz).

EXAMPLE 6

2-{2-[8a-(1H-Imidazol-4-yl)-5,6,7,8,8a,9-hexahydro-4bH-fluoren-3-yloxy]-ethoxy}-ethanol 2-{2-[8a-(1H-Imidazol-4-yl)-5,6,7,8,8a,g-hexahydro-4bH-fluoren-3-yloxy]ethoxy}ethanol was synthesised according to the procedure described in example 4i. 6-Fluoro-9a-(1H-imidazol-4-yl)-1,2,3,4,4a,9a-hexahydrofluoren-9-one was used as a starting material.

$^1$H NMR ($d_6$-DMSO): 1.22–1.46 (4H, m), 1.40 (1H, m), 1.81 (1H, m), 1.93(1H, m), 2.01 (1H, m), 2.83 (1H, d, J=14.9 Hz), 2.97 (1H, d, J=14.9 Hz), 3.52 (1H, bs), 3.63 (1H, m), 3.68 (2H, m), 3.77 (2H, m), 3.87 (2H, m), 4.14 (2H, m), 6.70 (1H, m), 6.78 (1H, s), 6.90 (1H, d, J=1.0 Hz), 7.08 (1H, m), 7.59 (1H, d, J=1.0 Hz).

EXAMPLE 7 a) 3-Bromoindan-1-one

1-Indanone (1 g) and NBS (1.4 g) was mixed with dry $CCl_4$ (20 ml). A catalytic amount of AIBN was added and the mixture was refluxed for 30 minutes and excited with light using 250 W lamp. The mixture was cooled in an ice bath and filtered. The filtrate was concentrated in an evaporator and used without further purification for the next step. Yield was 1.5 g.

$^1$H NMR ($d_6$-DMSO): 2.95 (1H, dd, J=19.6 Hz and 2.1 Hz), 3.51 (1H, dd, J=19.6 Hz and 7.0 Hz), 5.94 (1H, dd, J=7.0 Hz and 2.1 Hz), 7.58 (1H, m), 7.69 (1H, m), 7.77 (1H, m), 7.81 (1H, m).

b) Inden-1-one

3-Bromoindan-1-one (1.5) was dissolved in diethyl ether (10 ml). The temperature was kept at +2–+4 while TEA (2.7 ml) was added. The resulting mixture was further stirred at +2–+4 for 2 hours. The precipitated salt was filtered off and the filtrate evaporated. The crude inden-1-one was used for further reaction without purification. Yield was 0.9 g.

$^1$H NMR ($d_6$-DMSO): 5.99 (1H, d, J=6.0 Hz), 7.24 (1H, m), 7.28 (1H, m), 7.38 (1H, m), 7.45 (1H, m), 7.89 (1H, d, J=6.0 Hz).

c) 1,4-Ethano-1,4,4a,9a-tetrahydrofluoren-9-one (Diels-Alder reaction)

Inden-1-one (0.9 g) was dissolved in ethanol (5 ml) and added into the mixture of 1,3-cyclohexadiene (1.1 ml) and acetic acid (0.1 ml) in ethanol (5 ml). The mixture was stirred at the ambient temperature for 48 hours. Evaporation gave 1.4 g of the crude product which was used for the next step without further purification.

$^1$H NMR ($d_6$-DMSO): 1.27 (1H, m), 1.35 (1H, m), 1.66 (1H, m), 1.77 (1H, m), 2.73 (1H, dd, J=7.0 Hz and 3.3 Hz), 2.99 (1H, m), 3.06 (1H, m), 3.44 (1H, dd, J=7.0 Hz and 2.9 Hz), 5.68 (1H, m), 5.90 (1H, m), 7.36 (1H, m), 7.52 (1H, m), 7.65 (2H, m).

d) 1,4-Ethano-1,2,3,4,4a,9a-hexahydrofluoren-9-one 1,4-Ethano-1,4,4a,9a-tetrahydrofluoren-9-one (1.4 g) was dissolved in ethanol (10 ml). 10% Palladium on carbon catalyst was added and the mixture was hydrogenated at the room temperature until no more hydrogen was consumed (3 hours). The catalyst was filtered off and the solvent was removed under reduced pressure. The yield was 1.1 g of the crude product which was suitable for further reactions without purification.

$^1$H NMR ($d_6$-DMSO): 0.77 (1H, m), 1.04 (1H, m), 1.18 (2H, m), 1.65 (2H, m), 1.75 (2H, m), 2.06 (1H, m), 2.10 (1H, m), 2.68 (1H, m), 3.41 (1H, m), 7.46 (1H, m), 7.63–7.73 (3H, m).

e) 9a-(1H-Imidazol-4-yl)-1,4-ethano-2,3,4,4a,9,9a-hexahydro-1H-fluoren-9-ol

Hydroxy compound was synthesised as example 4e–h describes.

Recrystallization from $CH_2Cl_2$ gave the pure alcohol.

$^1$H NMR ($d_6$-DMSO): 0.94–1.42 (5H, m), 1.45–1.65 (3H, m), 2.10 (1H, m), 2.18 (1H, m), 3.70 (1H, m), 5.04 (1H, s), 5.55 (1H, bs), 6.92 (1H, bs), 7.22 (4H, m), 7.53 (1H, bs), 11.70 (1H, bs).

f) 4-(5,8-Ethano-4b,5,6,7,8,9-hexahydro-fluoren-8a-yl)-1H-imidazole 9a-(1H-Imidazol-4-yl)-1,4-ethano-2,3,4,4a,9,9a-hexahydro-1H-fluoren-9-ol (0.3 g) was converted to 4-(5,8-

Ethano-4b,5,6,7,8,9-hexahydro-fluoren-8a-yl)-1H-imidazole according to example 5. Yield was 0.25 g.

$^1$H NMR (d$_6$-DMSO): 0.95–1.80 (8H, m), 2.00 (1H, m), 2.04 (1H, m), 3.06 (1H, d, J=17.4 Hz), 3.51 (1H, d, J=17.4 Hz), 3.66 (1H, d, J=3.4 Hz), 7.21 (4H, m), 7.71 (1H, s), 9.11 (1H, s), 14.35 (1H, bs).

EXAMPLE 8

4-(4b,10-Dihydro-9H-indeno[1,2-a]inden-9a-yl)-1H-imidazole 4-(4b,10-Dihydro-9H-indeno[1,2-a]inden-9a-yl)-1H-imidazole was synthesised according to the procedure described in example 10. 2-Acetyl-1-indanone was used as a starting material.

$^1$H NMR (d$_6$-DMSO): 3.04 (2H, d, J=16.2 Hz), 3.46 (2H, d, J=16.2 Hz), 4.75 (1H, s), 6.92 (1H, s), 7.16 (6H, m), 7.39 (2H, m), 7.54 (1H, s), 11.75 (1H, s).

EXAMPLE 9 a) 2-Acetyl-2-benzyl-3,4-dihydro-2H-naphthalen-1-one

2-Acetyl-1-tetralone (5.0 g) was added into a mixture of potassium carbonate (3.8 g) and acetonitrile (60 ml). The mixture was stirred at 60° C. for 30 minutes and benzyl chloride was added and the stirring was continued at 60° C. for 5 hours. The mixture was filtered and evaporated. The yield was 7.2 g and was used for further reactions without purification.

$^1$H NMR (d$_6$-DMSO): 1.87 (1H, m), 2.20 (3H, s), 2.42 (1H, m), 2.85 (2H, m), 3.15 (1H, d, J=13.6 Hz), 3.36 (1H, d, J=13.6 Hz), 7.15–7.40 (7H, m), 7.53 (1H, m), 7.92 (1H, m).

b) 2-Benzyl-2-(2-bromoacetyl)-3,4-dihydro-2H-naphthalen-1-one

2-Benzyl-2-(2-bromoacetyl)-3,4-dihydro-2H-naphthalen-1-one was synthesised according to the procedure described in example 4f.

$^1$H NMR (d$_6$-DMSO): 1.94 (1H, m), 2.50 (1H, m), 2.88 (2H, m), 3.28 (1H, d, J=13.7 Hz), 3.37 (1H, d, J=13.7 Hz), 4.59 (1H, d, J=14.6 Hz), 4.71 (1H, d, J=14.6 Hz), 7.10–7.45 (7H, m), 7.55 (1H, m), 7.93 (1H, m).

c) 2-Benzyl-2-(1H-imidazol-4-yl)-3,4-dihydro-2H-naphthalen-1-one

2-Benzyl-2-(1H-imidazol-4-yl)-3,4-dihydro-2H-naphthalen-1-one was synthesised according to the procedure described in example 4g.

$^1$H NMR (d$_6$-DMSO): 1.96 (1H, m), 2.45 (1H, m), 2.83 (2H, m), 3.06 (1H, d, J=13.0 Hz), 3.37 (1H, d, J=13.0 Hz), 6.67 (1H, d, J=0.9 Hz), 6.95–7.35 (7H, m), 7.44 (1H, m), 7.56 (1H, d, J=0.9 Hz), 7.96 (1H, m).

d) 2-Benzyl-2-(1H-imidazol-4-yl)-1,2,3,4-tetrahydronaphthalen-1-ol

2-Benzyl-2-(1H-imidazol-4-yl)-1,2,3,4-tetrahydronaphthalen-1-ol was synthesised according to the procedure described in example 4h. Synthesis gave two diastereomers and were used for the next step without further purification.

$^1$H NMR (d$_6$-DMSO): 1.71 (1H, m), 2.14 (1H, m), 2.75 (2H, m), 2.94 (1H, d, J=12.9 Hz), 3.13 (1H, d, J=12.9 Hz), 4.55 (1H, s), 6.65–7.59 (11H, m).

e) 4-(5,6,7,11b-Tetrahydro-benzo[c]fluoren-6a-yl)-1H-imidazole

2-Benzyl-2-(1H-imidazol-4-yl)-1,2,3,4-tetrahydronaphthalen-1-ol (0.68 g) was dissolved in CH$_3$SO$_3$H (17 ml) and heated at 140° C. for 3 hours. After cooling in an ice bath, water (80 ml) was added and pH was adjusted to 11.5–13.5 with 48% NaOH solution. The precipitated crude product (0.41 g) was filtered and washed with water. An analytical sample was purified by flash chromatography using methylene chloride/methanol (95/5) as eluent.

$^1$H NMR (d$_6$-DMSO): 1.71 (1H, m), 2.06 (1H, m), 2.54 (2H, m), 3.01 (1H, d, J=15.6 Hz), 3.17 (1H, d, J=15.6 Hz), 4.67 (1H, s), 6.75 (1H, s), 7.01–7.48 (8H, m), 7.54 (1H, s).

The disclosures of all documents cited in this specification are incorporated by reference herein.

We claim:

1. A compound of formula (I):

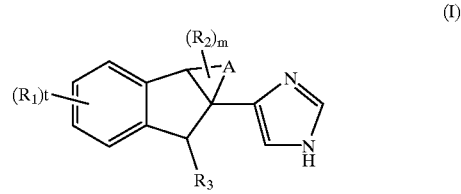

(I)

or a pharmaceutically acceptable ester or salt thereof, wherein,

—A— forms, together with the two carbon atoms to which it is attached, a ring system being a partially or fully saturated monocyclic carbocyclic ring of 3 to 7 ring atoms or a partially or fully saturated bicyclic bridged carbocyclic ring of 6 to 10 ring atoms, wherein each of the said ring systems formed by —A— is optionally fused with a benzene ring that is optionally substituted with one to three substituent(s) $R_1$;

each $R_1$ is independently halogen, OH, NH$_2$, (C$_{1-6}$)alkyl, (C$_{2-6}$)alkenyl, (C$_{2-6}$)alkynyl, (C$_{1-6}$)alkoxy, halo-(C$_{1-6}$)alkyl, OH—(C$_{1-6}$)alkyl, mono- or di(C$_{1-6}$)alkylamino or OH—(C$_{1-6}$)alkoxy(C$_{1-6}$)alkoxy;

each $R_2$ is independently halogen, OH, =O, =CH$_2$, NH$_2$, (C$_{1-6}$)alkyl, (C$_{2-6}$)alkenyl, (C$_{1-6}$)alkoxy, halo-(C$_{1-6}$)alkyl, OH—(C$_{1-6}$)alkyl, NH$_2$—(C$_{1-6}$)alkyl or mono- or di(C$_{1-6}$)alkylamino;

$R_3$ is H, F, OH, =O, =CH$_2$, (C$_{1-6}$)alkyl, (C$_{2-6}$)alkenyl, (C$_{2-6}$)alkynyl, (C$_{1-6}$)alkoxy, halo-(C$_{1-6}$)alkyl, NH$_2$ or mono- or di(C$_{1-6}$)alkylamino;

m is 0, 1, 2 or 3; and t is 0, 1, 2 or 3.

2. A compound according to claim 1, wherein m is 0.

3. A compound according to claim 1, wherein m is 1.

4. A compound according to claim 1, wherein $R_2$ is OH, =O, =CH$_2$, (C$_{1-6}$)alkyl or (C$_{1-6}$)alkoxy.

5. A compound according to claim 1, wherein t is 0.

6. A compound according to claim 1, wherein t is 1.

7. A compound according to claim 1, wherein $R_1$ is halogen, OH, (C$_{1-6}$)alkyl, (C$_{1-6}$)alkoxy or OH—(C$_{1-6}$)alkoxy(C$_{1-6}$)alkoxy.

8. A compound according to claim 1, wherein $R_3$ is H, F, OH, =O, =CH$_2$ or (C$_{1-6}$)alkyl.

9. A compound according to claim 1, which is a compound of formula Ia,

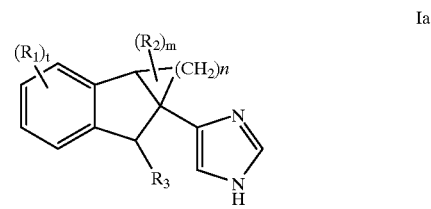

Ia or a pharmaceutically acceptable ester or salt thereof, wherein $R_1$, $R_2$, $R_3$, m and t are as defined in claim 1, and n is 1 to 5.

10. A compound according to claim 1, which is a compound of formula Ib

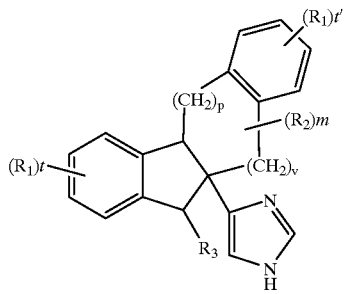

or a pharmaceutically acceptable ester or salt thereof, wherein $R_1$, $R_2$, $R_3$, m and t are as defined in claim 1; t' is 0, 1, 2 or 3; p is 0, 1, 2 or 3; and v is 0, 1, 2 or 3, with the proviso that p+v is 1, 2 or 3.

11. A compound according to claim 10, wherein m is 0, 1 or 2; p is 0 and v is 1 or 2.

12. A pharmaceutical composition, comprising at least one compound according to claim 1 and a pharmaceutically acceptable excipient.

13. A method for the treatment of a neurological, psychiatric or cognition disorder, of diabetes, of a lipolytic disorder, of orthostatic hypotension, or of sexual dysfunction, which comprises administering to a subject in need of such treatment an effective amount of at least one compound according to claim 1.

14. A mixture of two or more compounds as claimed in claim 1.

15. A mixture of two or more compounds as claimed in claim 9.

16. A mixture of two or more compounds as claimed in claim 10.

* * * * *